United States Patent
Tamper et al.

(10) Patent No.: US 10,858,330 B2
(45) Date of Patent: Dec. 8, 2020

(54) METHOD AND AN APPARATUS FOR SEPARATING FURFURAL

(71) Applicant: UPM-KYMMENE CORPORATION, Helsinki (FI)

(72) Inventors: Juha Tamper, Levänen (FI); Hans Hasse, Kaiserslautern (DE); Nadia Galeotti, Kaiseslautern (DE); Fabian Jirasek, Kaiserslautern (DE); Jakob Burger, Straubing (DE)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 16/473,355

(22) PCT Filed: Dec. 22, 2017

(86) PCT No.: PCT/FI2017/050929
§ 371 (c)(1),
(2) Date: Jun. 25, 2019

(87) PCT Pub. No.: WO2018/122453
PCT Pub. Date: Jul. 5, 2018

(65) Prior Publication Data
US 2020/0123120 A1  Apr. 23, 2020

(30) Foreign Application Priority Data
Dec. 30, 2016 (FI) ........................... 20166047

(51) Int. Cl.
*C07D 307/50* (2006.01)
*B01D 3/36* (2006.01)

(52) U.S. Cl.
CPC ............. *C07D 307/50* (2013.01); *B01D 3/36* (2013.01)

(58) Field of Classification Search
CPC ................................ C07D 307/50; B01D 3/36
USPC .............................................. 549/490; 203/86
See application file for complete search history.

(56) References Cited

U.S. PATENT DOCUMENTS

| | | |
|---|---|---|
| 2,369,655 A | 2/1945 | Boehm |
| 4,088,660 A | 5/1978 | Puurunen |

FOREIGN PATENT DOCUMENTS

| | | |
|---|---|---|
| WO | 2006/024242 A1 | 3/2006 |
| WO | 2009/130386 A1 | 10/2009 |
| WO | 2012/057625 A2 | 5/2012 |

(Continued)

OTHER PUBLICATIONS

International Search Report from International Application No. PCT/FI2017/050929 dated Feb. 16, 2018.
(Continued)

*Primary Examiner* — Taylor V Oh
(74) *Attorney, Agent, or Firm* — Nixon Peabody LLP

(57) ABSTRACT

In a method and an apparatus furfural is separated from a material stream (3) which is formed in a treatment of a pretreated wood based material (1). The material stream (3) which comprises at least furfural is introduced to a separation column (5). A top vapor condensate (6) is introduced from a top end of the separation column (5) to a decanter (10) in which two liquid phases (9,11) are separated from each other. An organic phase (9) which comprises at least furfural is recovered, and an aqueous phase (11) is supplied as a reflux to the separation column (5). Further, the invention relates to a furfural based product and chemical product and a use of the organic phase.

25 Claims, 1 Drawing Sheet

(56) References Cited

FOREIGN PATENT DOCUMENTS

WO 2016/020269 A1 2/2016

OTHER PUBLICATIONS

Search Report from Finnish Patent Application No. 20166047 dated Jul. 17, 2017.
L.C. Nhien, et al., "Design and optimization of intensified biorefinery process for furfural production through a systematic procedure" Biochemical Engineering Journal Apr. 5, 2016, vol. 116, 166-175.
Office Action from Patent Application No. 20166047 dated Dec. 14, 2018.
Reflux Definition—Wikipedia, Sep. 2016, https://en.wikipedia.org/wiki/Reflux.

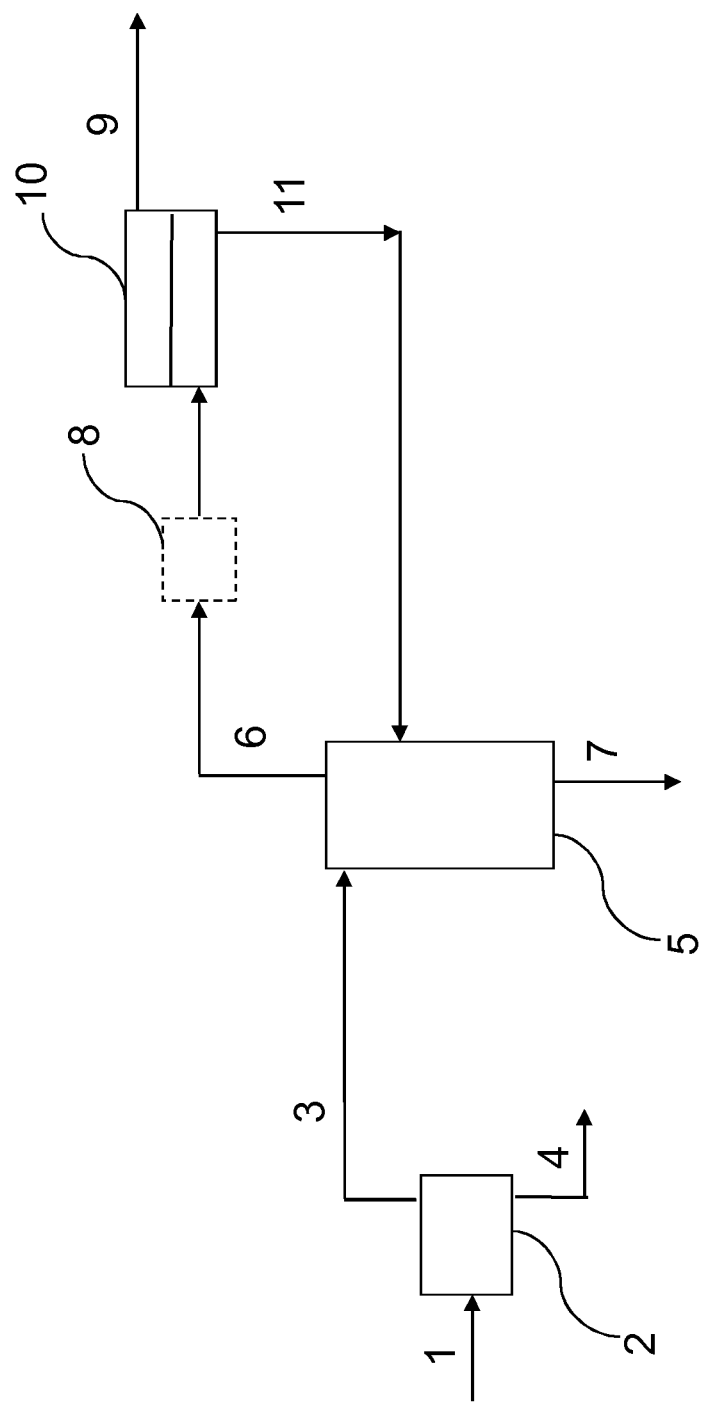

METHOD AND AN APPARATUS FOR SEPARATING FURFURAL

CROSS-REFERENCE TO RELATED APPLICATIONS

This application is a U.S. National Stage of International Application No. PCT/FI2017/050929, filed Dec. 22, 2017, which claims the benefit of Finnish Patent Application No. 20166047, filed Dec. 30, 2016, both of which are hereby incorporated by reference in their entireties.

FIELD

The invention relates to a method and an apparatus for separating furfural. Further, the invention relates to a furfural based product and a chemical product. Further, the invention relates to a use of organic phase.

BACKGROUND

It is known different methods for forming carbohydrates and lignin from different raw materials, such as biomass. Many bio-refinery processes, e.g. a hydrolysis, generate lignin and sugars after the treatment of the biomass. It is known that sugars streams comprise also other chemical compounds, e.g. furfural.

OBJECTIVE

The objective of the invention is to disclose a method for separating furfural. Another objective is to remove furfural from products formed in a treatment of wood based material. Another objective is to recover furfural from the wood based material. Another objective is to recover other chemical compound, such as carboxylic acid, from the wood based material.

SUMMARY

The method for separating furfural is characterized by what is presented in claim 1.

The apparatus for separating furfural is characterized by what is presented in claim 15.

The furfural based product is characterized by what is presented in claim 22.

The chemical product is characterized by what is presented in claim 23.

The use of the organic phase is characterized by what is presented in claim 24.

BRIEF DESCRIPTION OF THE DRAWINGS

The accompanying drawings, which are included to provide a further understanding of the invention and constitutes a part of this specification, illustrate some embodiments of the invention and together with the description help to explain the principles of the invention. In the drawings:

FIG. 1 is a flow chart illustration of a method according to one embodiment.

DETAILED DESCRIPTION

In a method for separating furfural from a material stream (3), which is formed in a treatment of a pretreated wood based material (1), the material stream (3) which comprises at least furfural is introduced to a separation column (5), a top vapor condensate (6) is introduced from a top end of the separation column (5) to a decanter (10) in which two liquid phases (9,11) are separated from each other, an organic phase (9) which comprises at least furfural is recovered, and an aqueous phase (11) is supplied as a reflux to the separation column (5).

One embodiment of the method is shown in FIG. 1.

The apparatus for separating furfural comprises at least one feeding device for introducing a material stream (3) which comprises at least furfural to a separation column (5), at least one separation column (5) in which at least a top vapor condensate (6) is formed, at least one decanter (10) to which the top vapor condensate (6) is introduced from a top end of the separation column (5) and in which two liquid phases (9,11) are separated from each other and from which an organic phase (9) which comprises at least furfural is supplied out and recovered, and at least one recirculating device for supplying an aqueous phase (11) from the decanter as a reflux to the separation column (5).

In this context, a material stream (3) means any material stream which is formed, e.g. by separating, collecting or recovering, from a pretreated wood based material (1) and which comprises at least furfural. The material stream (3) may comprise also organic acids, such as acetic acid or other organic acids. In one embodiment, the material stream comprises at least water, furfural and organic acids. The material stream may comprise also other components. In one embodiment, the material stream (3) may be the pretreated wood based material or, preferably, a fraction of the pretreated wood based material. In one embodiment, the material stream (3) may be formed from the pretreated wood based material after any suitable treatment stage of the pretreated wood based material. The material stream (3) may be in the form of steam, such as vapor, or liquid, such as condensate.

In one embodiment, the pretreated wood based material (1) comprises at least carbohydrates, such as C5 and/or C6 carbohydrates, and furfural. In one embodiment, the pretreated wood based material (1) comprises at least C5 carbohydrates. In one embodiment, the pretreated wood based material (1) comprises at least C5 and C6 carbohydrates. Further, in one embodiment, the pretreated wood based material comprises organic acids. Further, the pretreated wood based material (1) may comprise also other components, such as side and degradation products. In one embodiment, the pretreated wood based material (1) is formed from raw material. In one embodiment, the pretreated wood based material (1) is formed in a wood-to-sugar process. In one embodiment, the raw material comprises at least one of wood based material, wood, lignocellulosic biomass, agricultural residues, bagasse based material, sugarcane bagasse, corn based material, corn stover, wheat straw, rice straw, woody biomass, woody perennials, vascular plants, recycled brown board or deinking pulp, or their mixtures or their combinations. Preferably, the raw material is cellulose based material. The raw material may comprise lignin, lignocellulose, cellulose, hemicellulose, glucose, xylose and/or extractives. Further, the raw material may comprise other inherent structural components of biomass as well as foreign components such as enzymes or chemicals. In one embodiment, the raw material comprises wood based material or a mixture comprising wood based material. In one embodiment, the raw material is wood based material or a mixture comprising wood based material. In one embodiment, the wood based material is selected from hardwood, softwood or their combination. In one embodiment, the raw material comprises plant pieces, e.g. wood pieces. In one embodiment, the raw material comprises lignin, cellulose, carbohydrates and some chemical compounds. In one embodiment, the raw material may be treated by means of any suitable method for forming the pretreated wood based material (1). In one embodiment, the pretreated wood based material (1) is formed from the raw material which preferably is treated to dissolve at least a part of hemicellulose or a main part of hemicellulose. In one embodiment, the raw material is pre-treated, preferably by means of a suitable pretreatment stage which may be selected from the group comprising physical pretreatment, such as milling, extrusion, microwave pretreatment, ultrasound pretreatment and freeze pretreatment, chemical pretreatment, such as acid pretreatment, alkaline pretreatment, ionic liquid pretreatment, organosolv pretreatment and ozonolysis, physico-chemical pretreatment, such as steam explosion pretreatment, ammonia fiber explosion pretreatment, $CO_2$ explosion pretreatment, liquid hot water pretreatment and wet oxidation, biological pretreatment and their combinations. In one embodiment, the raw material is treated by the hydrolysis, e.g. acid hydrolysis, autohydrolysis, thermal hydrolysis, supercritical hydrolysis and/or subcritical hydrolysis, in which at least a part of hemicellulose is separated from the raw material in connection with the hydrolysis. In one embodiment, the raw material is treated by the steam explosion, in which hemicelluloses are treated and in which at least a part of polysaccharides of the hemicelluloses degrade into monosaccharides and oligosaccharides by means of a hydrolysis and in which pressure is rapidly released. In one embodiment, the raw material is treated by the hydrolysis and by the steam explosion in one or more steps. In one embodiment, the raw material is treated by the catalytic pretreatment, e.g. by using acid or base as catalyst. In the pretreatment stage the raw material enters the reactor unit where the pretreatment takes place. The raw material can be treated by means of one or more pretreatment. The treated raw material can be then supplied directly, via an intermediate step, via an additional treatment step or via an intermediate storage as a pretreated wood based material (1) to a desired treatment stage and/or to a furfural separation. Further, in one embodiment, the raw material can be dewatered, e.g. by dewatering presses, and/or washed in one or two or more stages. The dewatering makes possible to separate sugar based streams.

In one embodiment, the pretreated wood based material (1) is supplied to a concentration stage (2) for forming a concentrated carbohydrate based material (4) and the material stream (3). The pretreated wood based material (1) may be treated in one or more than one concentration stage (2). The material stream may be in the form of steam or liquid after the concentration stage (2). In one embodiment, the material stream (3) is a vapor or a condensate of vapor from the concentration stage (2). In one embodiment, the material stream (3) is a top vapor of the concentration stage (2). Preferably, furfural accumulates into the material stream (3) during the concentration stage (2). In one embodiment, apparatus comprises at least one concentration stage (2) which comprises at least one concentration device and in which the pretreated wood based material is concentrated in order to form the concentrated carbohydrate based material (4) and the material stream (3). In one embodiment, apparatus comprises more than one concentration stage (2) which comprises at least one concentration device. In one embodiment, apparatus comprises more than one concentration devices. In one embodiment, the concentration stage (2) is an evaporation stage, e.g. a vacuum evaporation, multi-effect evaporation, forced circulation evaporation, film evaporation, or other suitable evaporation or their combinations. In one embodiment, the concentration stage (2) comprises at least one evaporation device. In one embodiment, the evaporation device is selected from the group comprising a vacuum evaporation device, mechanical vapor compressor, thermal vapor compressor, multi-effect evaporation device, forced circulation evaporation device, film evaporator, plate type evaporator, tube evaporator, batch evaporator, continuous evaporator and their combinations.

In this context, the concentrated carbohydrate based material (4) comprises at least C5 carbohydrates. In one embodiment, the concentrated carbohydrate based material (4) comprises C5 and C6 carbohydrates. The concentrated carbohydrate based material (4) may comprise also other agents or components. In one embodiment, the concentrated carbohydrate based material (4) is further concentrated by means of the top vapor condensate (6) after the separation column (5) in a post-evaporation stage.

The material stream (3) is introduced to the separation column (5). In one embodiment, the material stream (3) is fed to the separation column (5) at temperature of 70-80° C. The material stream (3) may be introduced to any suitable part of the separation column. In one embodiment, the material stream (5) is introduced to the top part of the separation column (5). In one embodiment, the material stream (5) is introduced to the bottom part of the separation column (5). In one embodiment, the material stream (5) is introduced to the middle part of the separation column (5). In one embodiment, the separation column (5) comprises trays or plates. In one embodiment, the separation column (5) comprises 5-20 stages or trays. In one embodiment, the separation column (5) comprises one or more than one columns.

In one embodiment, the separation column (5) is based on a hetero-azeotropic distillation. In one embodiment, an azeotropic mixture comprises at least furfural and water. In one embodiment, the separation column (5) is a hetero-azeotropic distillation device. In the hetero-azeotropic distillation two liquid phases are on the plate. The top vapor condensate (6) splits in two liquid phases which can be separated in the decanter (10). In one embodiment, the top vapor condensate (6) comprises at least furfural and water. In one embodiment, the hetero-azeotropic distillation is a batch distillation process. In one embodiment, the hetero-azeotropic distillation is a continuous distillation process.

In one embodiment, the material stream (3) is introduced to the separation column (5) in counter-current to a vapor formed in the separation column (5). In one embodiment, the vapor strips out furfural from the material stream leading to an increased concentration of furfural at the top end of the separation column (5).

In one embodiment, the temperature in the separation column (5) is 90-130° C., in one embodiment 95-105° C. and in one embodiment 115-125° C. In one embodiment, the pressure in the separation column (5) is 0.5-2.5 bar, in one embodiment 0.5-1.5 bar and in one embodiment 1.5-2.5 bar.

In one embodiment, a by-product (7) is discharged out from the separation column (5). In one embodiment, the by-product (7) is discharged from the bottom end of the separation column (5). The by-product (7) may comprise water, e.g. washing water or dilution water, and/or organic acids, e.g. acetic acid. In one embodiment, the by-product (7) is a water based stream. In one embodiment, the by-product (7) is a residue from the distillation.

In one embodiment, at least one carboxylic acid fraction is recovered in the separation column (5). In one embodiment, an acetic acid fraction is recovered in the separation column (5). The carboxylic acid fraction may be recovered from the bottom of the separation column (5) or from any suitable part, such as from a desired tray or plate, of the separation column (5).

In one embodiment, the top vapor condensate (6) is cooled in a cooling stage (8) before the decanter (10). In one embodiment, the apparatus comprises at least one cooling device (8) in which the top vapor condensate (6) is cooled before the decanter (10). The cooling device may be any suitable cooling device, e.g. a heat exchanger or condenser.

Preferably, in the decanter (10) the top vapor condensate (6) splits in two liquid phases. In one embodiment, the top vapor condensate (6) is supplied to a bottom part of the decanter (10). In one embodiment, temperature is 20-30° C., in one embodiment 23-28° C., during the decantation in the decanter (10). In one embodiment, pressure is 0.5-2.5 bar, in one embodiment 0.5-1.5 bar, in one embodiment 1.5-2.5 bar, during the decantation in the decanter (10). In one embodiment, the organic phase (9) is recovered from an upper part of the decanter and the aqueous phase (11) is discharged from the bottom part of the decanter. In one embodiment, the separation surface of the organic phase (9) and the aqueous phase (11) is adjusted to a suitable level during the decantation in the decanter (10). Preferably, the organic phase (9) comprises furfural in high purity, i.e. the organic phase is a furfural rich phase. In one embodiment, by means of the ratio of the organic phase (9) and the aqueous phase (11) and by means of the process conditions can be adjusted the purity of the organic phase (9).

In one embodiment, the apparatus comprises at least one recovery device for recovering the organic phase (9) which comprises at least furfural. Any suitable device can be used as the recovery device. In one embodiment, the recovery device is selected from the group comprising assembly, outlet, pipe, tube, duct, discharge outlet, discharge valve, discharge channel, conduit, other suitable device, tank, vessel and their combinations.

In one embodiment, the apparatus comprises at least one furfural purification stage comprising at least one purification device after the decanter (10) in which the organic phase (9) is purified and/or concentrated. In one embodiment, the purification device may be an additional distillation device or the second separation column (5), e.g. hetero-azeotropic distillation device, or other suitable device.

In one embodiment, the organic phase (9) comprises furfural over 70% by weight, preferably over 80% by weight, more preferably over 90% by weight and most preferably over 95% by weight.

The aqueous phase (11) is recirculated to the separation column (5). The aqueous phase (11) may comprise water and organic acids, such as acetic acid. Further, in one embodiment, the aqueous phase (11) may comprise also furfural. Any suitable device can be used as the recirculating device. In one embodiment, the recirculating device is selected from the group comprising assembly, pump, outlet, inlet, pipe, tube, duct, discharge outlet, discharge valve, discharge channel, conduit, other suitable feeding device, other suitable device and their combinations.

In one embodiment, the aqueous phase (11) is supplied as the reflux to the separation column (5) in counter-current to the material stream (3).

In one embodiment, the method is based on a continuous process. In one embodiment, the apparatus is a continuous apparatus. In one embodiment, the method is based on a batch process. In one embodiment, at least a part of the apparatus is a batch apparatus.

A furfural based product may be formed according to any method or apparatus defined above. In one embodiment, the furfural based product is in the form of liquid.

A chemical product comprising a carboxylic acid fraction may be formed according to any method or apparatus defined above. In one embodiment, the chemical product is in the form of liquid.

The organic phase (9) may be used as a source material in an additional treatment, chemical treatment, polymerization process, manufacture of a chemical, plastic, cellulose acetate or varnish, or other suitable process, or as a component in a fuel or combustion material, or their combinations.

The method and the apparatus provide furfural and also carbohydrates with good quality. By means of the method and apparatus carbohydrate based streams can be purified and waste water treatment plant loading can be reduced and valuable components can be recovered.

The method and the apparatus provide an industrially applicable, simple and affordable way of separating and recovering furfural and recovering also other chemicals. The method or the apparatus is easy and simple to realize as a production process. The method and the apparatus are suitable for use in connection with the manufacture of the different lignin and carbohydrate products from different raw materials.

EXAMPLES

Some embodiments of the invention are described in more detail by the following examples with reference to accompanying drawing.

Example 1

In this example, furfural is separated from a material stream (3) according to a process of FIG. 1.

The material stream (3) has been formed in a treatment of a pretreated wood based material (1) comprising at least carbohydrates and furfural. The pretreated wood based material has been formed from raw material by pretreating the raw material. The raw material is wood based material or a mixture comprising wood based material. The material stream (3) is in the form of steam or liquid.

The apparatus for separating furfural comprises at least one feeding device for introducing a material stream (3) which comprises at least furfural to a separation column (5), at least one separation column (5) in which at least a top vapor condensate (6) is formed, and at least one decanter (10) to which the top vapor condensate (6) is introduced from a top end of the separation column (5) and in which two liquid phases (9,11) are separated from each other. Further, the apparatus comprises at least one recovery device for recovering an organic phase (9) which comprises at least furfural and at least one recirculating device for supplying an aqueous phase (11) as a reflux to the separation column (5).

The separation column (5) is preferably based on a hetero-azeotropic distillation in which an azeotropic mixture comprises at least furfural and water.

The top vapor condensate (6) comprises at least furfural and water. Carboxylic acid fraction or fractions may be recovered in the separation column (5). Further, a by-product (7) may be discharged out from the separation column (5). The by-product (7) may comprise water and/or organic acids, e.g. acetic acid.

Preferably, the material stream is introduced to the separation column (5) in counter-current to a vapor formed in the separation column (5). Preferably, the aqueous phase (11) is supplied as the reflux to the separation column (5) in counter-current to the material stream (3).

Further, the apparatus may comprise a cooling device (8) in which the top vapor condensate (6) is cooled before the decanter (10).

Further, the apparatus comprise at least one concentration stage (2) comprising at least one concentration device, e.g. an evaporation device, in which the pretreated wood based material is concentrated in order to form a concentrated carbohydrate based material (4) and the material stream (3). The material stream (3) is collected during the concentration. The material stream may be a vapor or a condensate of vapor from the concentration device.

Further, the apparatus may comprise at least one furfural purification stage comprising at least one purification device after the decanter (10) in which the organic phase (9) is purified or concentrated.

Example 2

In this example, a furfural separation was studied.

The furfural was separated from a material stream (3) according to the process presented in FIG. 1.

A pretreated wood based material (1), 80 t/h, comprising at least C5 carbohydrates, such as xylose 50 g/l, and 0.4 w-% (4 g/l) furfural, was supplied to an evaporation stage (2) which comprises at least one evaporation device. The pretreated wood based material was formed from raw material by pretreating with diluted acid the raw material which is wood based material.

In the evaporation stage (2) the pretreated wood based material was treated and concentrated in order to form about 43.5 t/h concentrated carbohydrate based material (4) and about 36.5 t/h material stream (3) which comprises at least furfural. The pressure in the evaporation stage was about 0.5 bar. The material stream (3) was collected during the concentration. The material stream was in the form of a vapor after the evaporation device. The temperature of the material stream after the evaporation device was 81.30° C.

The material stream (3) which comprises at least furfural was introduced by means of a feeding device to a separation column (5) which is a hetero-azeotropic distillation column. A diameter of the distillation column was about 3 meters, and the distillation column comprised 15 stages. Temperature was 99.34° C. in a top part of the distillation column and 99.98° C. in a bottom part of the distillation column. Pressure was about 1.0 bar in the distillation column. In the separation column (5) a top vapor condensate (6) was formed. An azeotropic mixture comprised at least furfural and water. The top vapor condensate (6) comprised at least furfural and water. Carboxylic acid fraction or fractions may be recovered in the separation column (5). Further, a by-product flow (7) which is a water based flow was discharged out from the bottom of the separation column (5).

The top vapor condensate (6) was introduced from a top end of the separation column (5) to a cooling device (8) in which the top vapor condensate (6) was cooled. The temperature of the condensate (6) was 50° C. after the cooling device (8). After the cooling the condensate (6) was introduced to a decanter (10) in which two liquid phases, i.e. an organic phase (9) and an aqueous phase (11), were separated from each other. The organic phase (9) which comprises mainly furfural was recovered. The organic phase contained 92.1 w-% furfural The aqueous phase (11) which comprises mainly water was recirculated as a reflux to the separation column (5).

The material stream was introduced to the separation column (5) in counter-current to a vapor formed in the separation column (5). Further, the aqueous phase (11) was supplied as the reflux to the separation column (5) in counter-current to the material stream (3).

Further, the organic phase (9) may be purified by means of at least one furfural purification device after the decanter (10).

The method and apparatus according to the present invention is suitable in different embodiments to be used in different furfural separation processes and/or chemical recovery processes. Further, the method and apparatus according to the present invention is suitable in different embodiments to be used for producing the most different kinds of carbohydrate fractions and chemical products from different raw materials.

The invention is not limited merely to the example referred to above; instead many variations are possible within the scope of the inventive idea defined by the claims.

The invention claimed is:

1. A method for separating furfural from a material stream, the material stream being formed in a treatment of a wood based material, the method comprising:
   supplying the wood based material including at least C5 carbohydrates and furfural to a concentration stage for forming a concentrated carbohydrate based material including at least C5 carbohydrates and the material stream in which furfural accumulates into the material stream during the concentration stage;
   introducing the material stream, which comprises at least furfural, to a separation column;
   introducing a top vapor condensate from a top end of the separation column to a decanter in which two liquid phases are separated from each other;
   recovering an of organic phase, which comprises at least furfural;
   supplying an aqueous phase as a reflux to the separation column.

2. The method according to claim 1, wherein the material stream is in the form of steam or liquid.

3. The method according to claim 1, wherein the concentration stage is an evaporation stage.

4. The method according to claim 1, wherein the material stream is introduced to the separation column in counter-current to a vapor formed in the separation column.

5. The method according to claim 1, wherein the separation column is based on a hetero-azeotropic distillation.

6. The method according to claim 5, wherein an azeotropic mixture comprises at least furfural and water.

7. The method according to claim 1, wherein the top vapor condensate comprises at least furfural and water.

8. The method according to claim 1, further comprising recovering at least one carboxylic acid fraction in the separation column.

9. The method according to claim 1, further comprising cooling the top vapor condensate in a cooling stage before the decanter.

10. The method according to claim 1, wherein the organic phase comprises furfural over 70% by weight.

11. The method according to claim 1, wherein the aqueous phase is supplied as the reflux to the separation column in counter-current to the material stream.

12. The method according to claim 1, wherein the wood based material is formed from raw material, which is a wood based material or a mixture comprising wood based material.

13. An apparatus for separating furfural from a material stream, the material stream being formed in a treatment of a wood based material, the apparatus comprising:
- at least one concentration stage including at least one concentration device and in which the wood based material comprising at least C5 carbohydrates and furfural is concentrated to form a concentrated carbohydrate based material comprising at least C5 carbohydrates and the material stream and in which furfural accumulates into the material stream during the concentration stage;
- at least one feeding device for introducing the material stream, which comprises at least furfural, to a separation column;
- at least one separation column in which at least a top vapor condensate is formed;
- at least one decanter to which the top vapor condensate is introduced from a top end of the separation column and in which two liquid phases are separated from each other and from which an organic phase, which comprises at least furfural, is supplied out and recovered; and
- at least one recirculating device for supplying an aqueous phase as a reflux to the separation column.

14. The apparatus according to claim 13, wherein the concentration stage comprises at least one evaporation device.

15. The apparatus according to claim 13, wherein the separation column is a hetero-azeotropic distillation device.

16. The apparatus according to claim 13, further comprising at least one cooling device in which the top vapor condensate is cooled before the decanter.

17. The apparatus according to claim 13, further comprising at least one recovery device for recovering the organic phase, which comprises at least furfural.

18. The apparatus according to claim 13, further comprising at least one furfural purification stage after the decanter, in which the organic phase is purified and/or concentrated.

19. A method of forming an organic phase, the method comprising:
- supplying wood based material including at least C5 carbohydrates and furfural to a concentration stage for forming a concentrated carbohydrate based material including at least C5 carbohydrates and a material stream in which furfural accumulates into the material stream during the concentration stage;
- introducing the material stream, which comprises at least furfural, to a separation column;
- introducing a top vapor condensate from a top end of the separation column to a decanter in which two liquid phases are separated from each other; and
- recovering the organic phase, which comprises at least furfural,
- wherein the organic phase is for use as a source material in an additional treatment, chemical treatment, polymerization process, manufacture of a chemical, plastic, cellulose acetate or varnish, or other suitable process, or as a component in a fuel or combustion material, or any combination thereof.

20. The method of claim 1, wherein the wood based material is pretreated via physical pretreatment, ultra-sound pretreatment, freeze pretreatment, chemical pretreatment, physico-chemical pretreatment, biological pretreatment, and any combination thereof.

21. The method of claim 1, wherein the wood based material is pretreated using hydrolysis, steam explosion, or the combination thereof.

22. The method of claim 1, wherein the wood based material is pretreated using catalytic pretreatment.

23. The method of claim 19, wherein the wood based material is pretreated via physical pretreatment, ultra-sound pretreatment, freeze pretreatment, chemical pretreatment, physico-chemical pretreatment, biological pretreatment, and any combination thereof.

24. The method of claim 19, wherein the wood based material is pretreated using hydrolysis, steam explosion, or the combination thereof.

25. The method of claim 19, wherein the wood based material is pretreated using catalytic pretreatment.

* * * * *

UNITED STATES PATENT AND TRADEMARK OFFICE
CERTIFICATE OF CORRECTION

Page 1 of 1

PATENT NO. : 10,858,330 B2
APPLICATION NO. : 16/473355
DATED : December 8, 2020
INVENTOR(S) : Juha Tamper et al.

It is certified that error appears in the above-identified patent and that said Letters Patent is hereby corrected as shown below:

In the Claims

At Column 8, Line 36 (Claim 1, Line 15), please delete "an of organic phase" and insert --an organic phase-- therefor.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*